United States Patent [19]
Neill et al.

[11] Patent Number: 5,375,477
[45] Date of Patent: Dec. 27, 1994

[54] WATER IMPURITY EXTRACTION DEVICE AND METHOD

[75] Inventors: Norman A. Neill; David Cross, both of Vineland, N.J.

[73] Assignee: S.P. Industries, Limited Partnership, Buena, N.J.

[21] Appl. No.: 212

[22] Filed: Jan. 4, 1993

[51] Int. Cl.$^5$ .............................................. G01N 1/00
[52] U.S. Cl. .................. 73/863.23; 210/406; 137/883
[58] Field of Search ........... 73/863.31, 863.23, 863.24, 73/863.25; 210/321.6, 321.69, 321.72, 321.73, 321.75, 406, 416.1, 418, 419, 435–437, 441, 445, 446, 451, 453, 455, 473, 474, 477; 137/625.17, 625.42, 861, 862, 883, 887

[56] References Cited

U.S. PATENT DOCUMENTS

| | | | |
|---|---|---|---|
| 391,328 | 10/1888 | McTighe | 137/861 |
| 667,188 | 2/1901 | Clavez | 137/883 |
| 1,968,390 | 7/1934 | Hamilton | 137/887 |
| 2,755,935 | 7/1956 | Richards | 210/406 |
| 2,874,843 | 2/1959 | Townsend | 210/406 |
| 3,362,222 | 1/1968 | Johnson et al. | 73/198 |
| 3,524,351 | 8/1970 | Bayly et al. | 73/421 |
| 3,730,352 | 5/1973 | Cohen et al. | 210/406 |
| 3,846,075 | 11/1974 | Cioffi | 23/253 |
| 3,956,125 | 5/1976 | Strutt et al. | 210/406 |
| 4,247,399 | 1/1981 | Pitesky | 210/406 |
| 4,655,094 | 4/1987 | Herzfeldt | 73/863.31 |
| 5,005,430 | 4/1991 | Kibler et al. | 73/863.01 |
| 5,012,681 | 5/1991 | Lentzen | 73/863.23 |

OTHER PUBLICATIONS

Feb. 1991 J. T. Baker 3M Empore TM Extraction Disks with Bakerbond TM C$_{18}$ & C$_8$.
Feb. 1991 J. T. Baker Run More Water Quality Tests in Less Time Using Less Solvent.
Feb. 1991 J. T. Baker Empore TM Extraction Disks with Bakerbond Bonded Phases.
CPC Couplings pp. 4 & 5 Colder Products Co.

Primary Examiner—Robert Raevis
Attorney, Agent, or Firm—Thomas A. Lennox

[57] ABSTRACT

A device to facilitate the use of extraction discs used in analysis of water impurities includes a cylindrical body with a top cavity to receive the extraction disc with a threaded ring holder to hold an open bottom container sealed on the extraction disc with a valve to selectively channel flow from the extraction disc into three downward passages, two of which open through the bottom into wash and elute sample containers and a third to a tube that opens into a large collection container sealably attached to the bottom of the body around the smaller containers with a vacuum passage through the bottom of the body into the large container controlled by a valve. The body has two parallel slots on opposite sides of the body to engage into cut outs of a rack panel supported above a housing with a slanted top wall with elliptical holes cut to receive the collection container and support it sticking out of the housing.

23 Claims, 5 Drawing Sheets

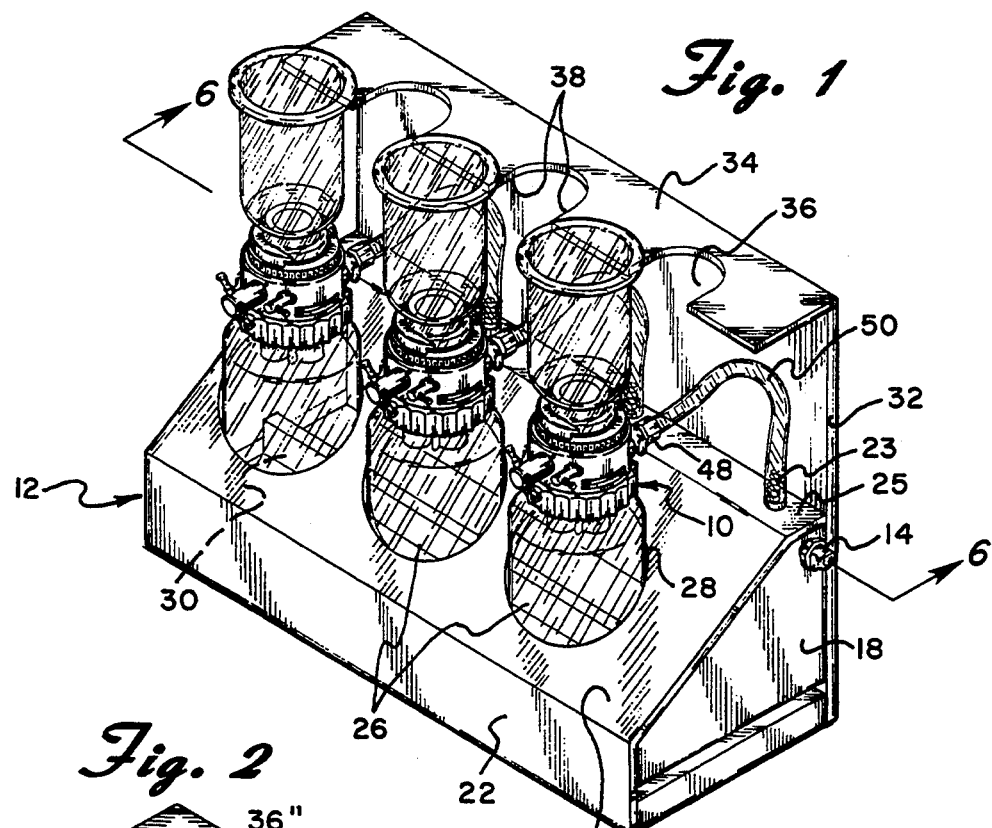
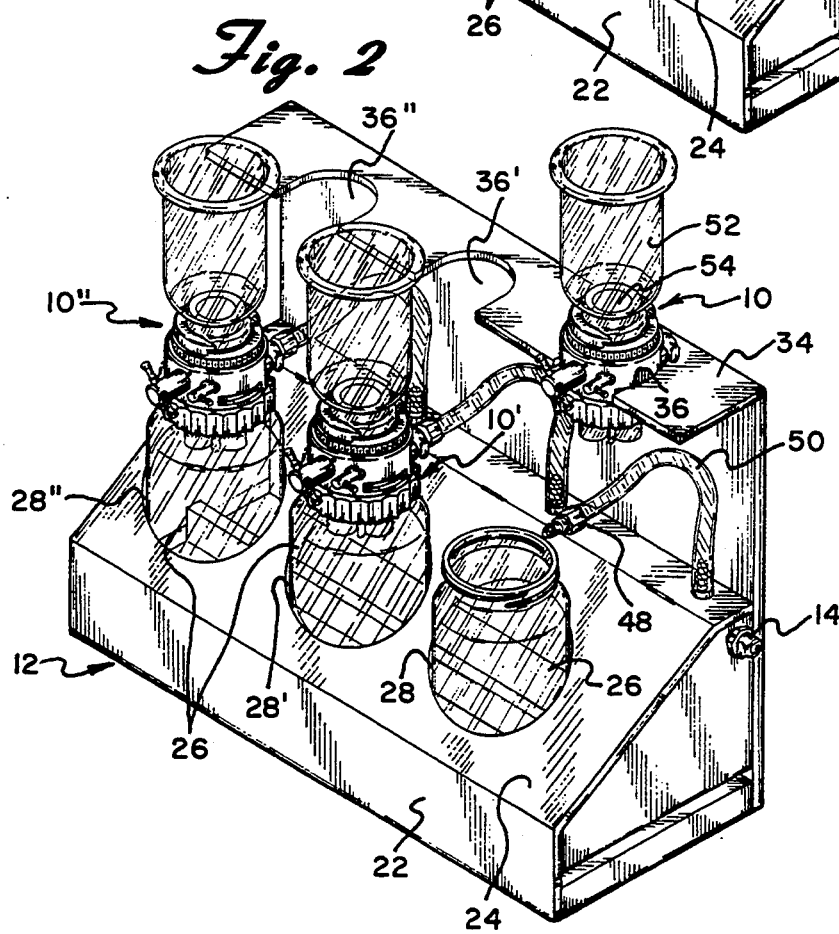

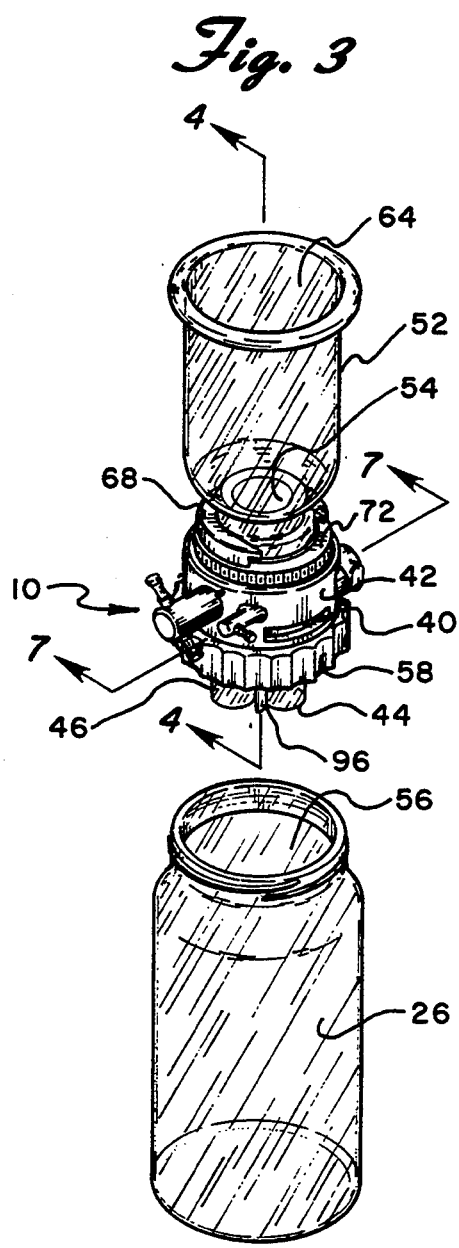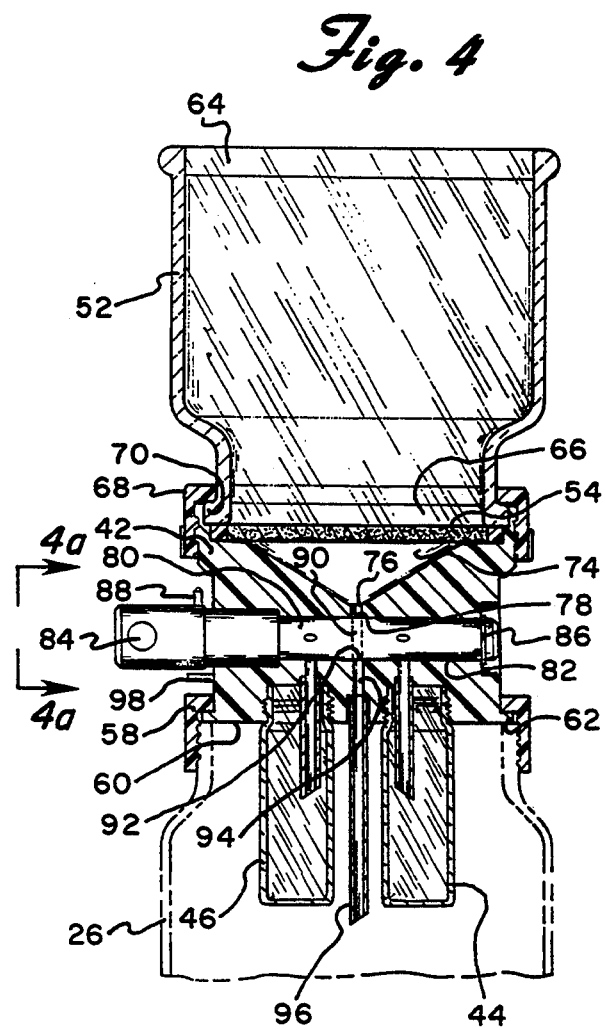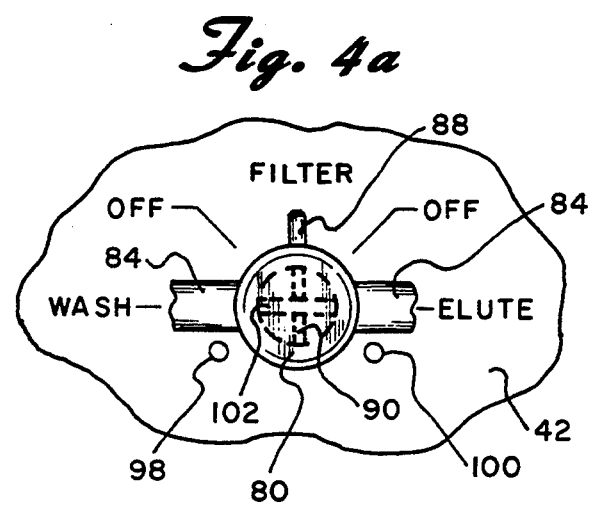

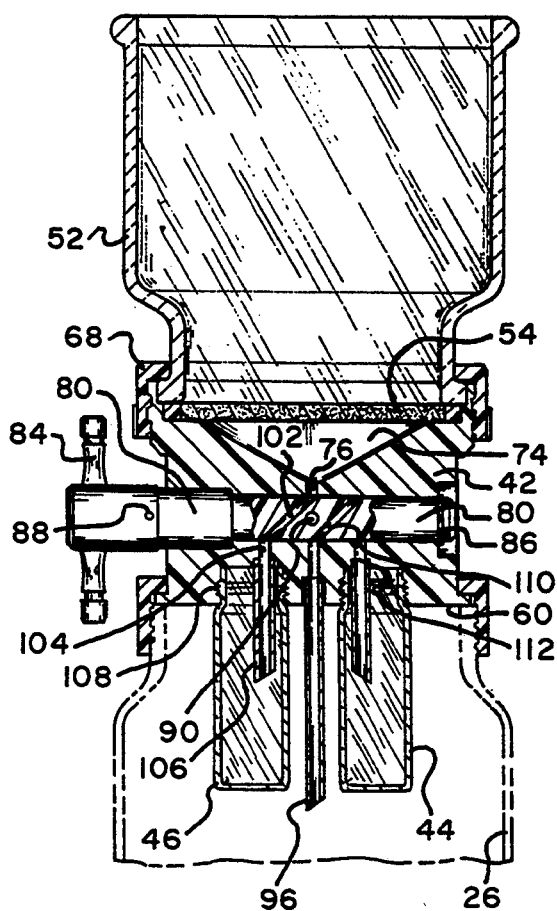
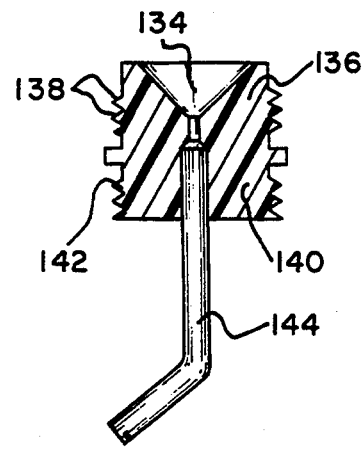
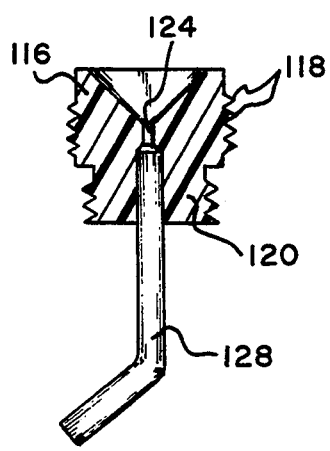
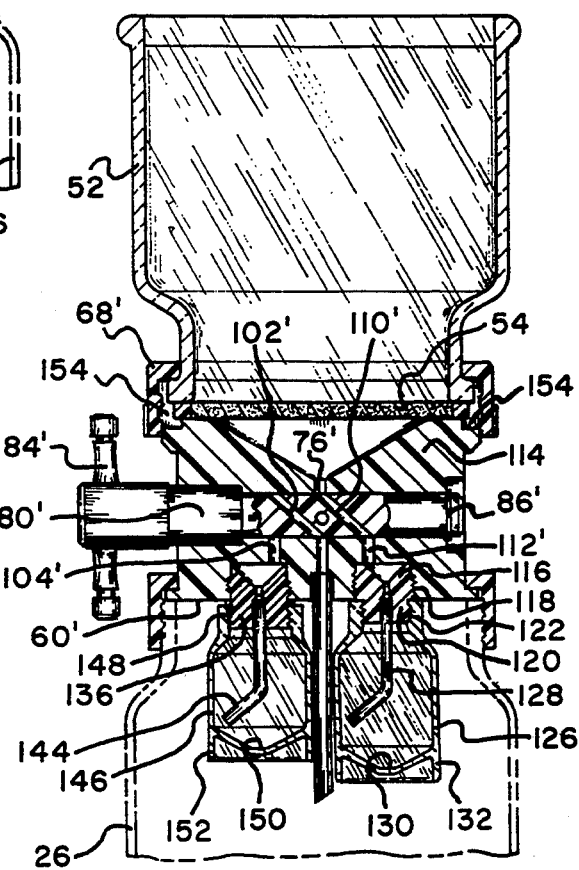

WATER IMPURITY EXTRACTION DEVICE AND METHOD

BACKGROUND OF THE INVENTION

This invention involves a device and apparatus to utilize extraction discs to collect and measure impurities in liquids, specifically water. This invention also involves a method of handling apparatus together with mechanisms to carry out the extraction of impurities.

The testing of the purity of drinking water in particular the determination of the presence and quantity of minute quantities of a very large number of possible contaminants is saddled with high costs of testing. These high costs are in large measure due to the multitude of separate steps, the difficulty of handling the glassware to maintain absolute cleanliness and the rather labor intensive testing procedures involved.

EMPORE TM extraction discs marketed by J. T. Baker, Inc. and J. T. Baker B. V. 222 Redschool Lane, Phillipsburg, N.J. 0885 are a relatively new sample extraction product. The EMPORE TM discs are supplied by the 3M Company and are bonded to handling discs by J. T. Baker. These extraction discs and methods provided to handle and use these discs in the extraction procedures are described in the Feb. 1991 J. T. Baker bulletins and brochures entitled "3M EMPORE TM EXTRACTION DISKS WITH BAKERBOND TM $C_{18}$ AND $C_8$", "RUN MORE WATER QUALITY TESTS IN LESS TIME USING LESS SOLVENT", and "i EMPORE TM EXTRACTION DISKS WITH BAKERBOND BONDED PHRASES" l all incorporated herein by reference thereto.

The determination of organic compounds in drinking water by a liquid-solid extraction methods are described in publication method 525.1 titled *Determination of Organic Compounds in Drinking Water by Liquid-Solid Extraction and Capillary Column Gas Chromatography/Mass Spectrometry* Revision 2.2 J. W. Eichelberger, Et al, method 525, Revision 1.0, 2.0, 2.1 (1988) published by Environmental Monitoring Systems Laboratory Office of Research and Development, United States Environmental Protection Agency, Cincinnati, Ohio 45268 pages 325 through 361 et sec, all incorporated herein by reference thereto.

The EMPORE TM sample extraction products include chemically bonded silica enmeshed at an inert polytetrafluoroethylene to create a mechanically stable sorbent disc. These discs provide substantial improvement in the extraction procedure reducing the time-consuming mixing and shaking operations of large volumes of solvents. The well recognized time-consuming procedures of liquid/liquid extraction are improved by the rapid extraction of analytes coupled with low solvent usage and accurate analysis.

While the EMPORE TM extraction discs greatly reduce the time required for these tests, the time and cost comparison provided by the supplier still indicates that there is a substantial cost and time commitment to these tests. Prior to the use of these discs, the time required for testing was estimated by J. T. Baker, Inc., in the brochures incorporated hereinabove, at five hours with a cost of three hundred and six dollars. Even with the EMPORE TM discs the time required was admitted to be 1.7 hours with a cost of one hundred and fifty six dollars. The photographs incorporated in the referenced bulletins showing the glassware utilized for each step and extraction as well as multiple glassware for the multiple tests required attest to the major problem of handling the samples, the glassware and the methods involved. There is a clear need to streamline the procedures and reduce the time and expense involved in these testing procedures.

None of the prior art devices and methods, including U.S. Pat. No. 5,012,681 to LENTZEN; 5,005,430 to KIBLER ET AL; 4,655,094 to HERZFELDT; 3,846,075 to CIOFFI; 3,524,351 to BAYLY ET AL; and 3,362,222 to JOHNSON ET AL, provide a suitable answer to the handling difficulties and the time involved in the testing procedures or attain the objects described hereinbelow.

SUMMARY OF THE INVENTION

It is an object of the present invention to provide an extraction device and method that essentially eliminates the possibility of contamination of the samples, glassware and equipment used in the extraction process.

An additional object of the present invention is to provide an apparatus and method which makes it extremely difficult, for an error in handling to jeopardize the accuracy of the results.

It is an important object of the invention to provide a device and method that allows the solvent used to prewash the extraction disc to be separately collected for re-use or disposal rather than mixing it with the water sample passing through the extraction disc.

It is a further object of the invention to provide a device and method that allows vacuum to be drawn and controlled by a single valve on all of the liquid collection at the same time.

It is an additional object of the present invention to provide an apparatus and method wherein it is virtually impossible to interchange the containers of the sample to be analyzed with wash samples and other liquids resulting from the extraction process.

It is an object of the present invention to provide an apparatus and method wherein the various steps of prewash of the filter, collection of the analyte on the extraction disc, and collecting the analyte in a liquid sample all without breaking the seal or changing glassware.

It is an object of the present invention to provide an apparatus wherein multiple samples can be simultaneously extracted.

It is a further object of the present invention to provide an apparatus and method wherein collection of the samples after extraction can be carried out without separate handling steps or the necessity of laying glassware on the table or bench.

It is a particular object of the present invention to provide an apparatus and method which substantially reduces personnel handling and time carrying out the extraction and readying the equipment for the next sample.

It is additional object of the present invention to provide an apparatus that is safe to use reducing the likelihood of injury due to glass breakage and vacuum.

It is a specific object of the present invention to provide sample containers with great resistance to contamination during the closure and sealing process as well as the removal of the sample for gas chromatography and spectrometry testing procedures.

An aspect of the invention is a device to collect liquid samples of compounds. The device includes a body that include an inlet to receive liquid flow and a bottom portion comprising a bottom surface. The device further includes channeling means in the body to selectively channel liquid flow through the body to a chosen one of three openings through the bottom surface and first container holding means to hold an open top container to the bottom of the body and to seal said open top over the bottom surface. The device also includes second container holding means to hold at least two open top sample containers to the bottom surface of the body aligning each of said open tops to receive liquid flow from only one of the three openings through the bottom surface. The device further includes guide means to guide flow out of a remaining opening of the three openings through the bottom surface past the sample containers to the open top container and vacuum means to selectively connect a vacuum source to the open top container.

It is preferred that the body further include a top and a cavity opening to the top of sufficient size and shape to receive and hold an extraction disc in a horizontal position. It is further preferred that the device further include first container holding means to hold an open bottom container on the top of the body and to seal the open bottom around the cavity opening. It is also preferred that the channeling means include a single first passage in the body from the inlet to an orifice opening to a first valve means to selectively direct liquid flow out of the orifice to a chosen opening to one of three second passages through the body, each of the second passages opening to one of the three openings through the bottom surface. It is further preferred that the vacuum means include a third passage through the body from an opening on a side of the body connectable to a vacuum source, the passage continuing to an opening through the bottom surface of the body and second valve means to selectively open or close the third passage. It is further preferred that the first valve means include a circular rod stem rotatable to chosen radial positions in the body with three fourth passage laterally through the stem, wherein one end of each fourth passage is alignable with only one of the second passages while at the same time an opposite end of the aligned fourth passage is in flow connection with the first passage. It is further preferred that the second container holding means allows each of the open topped sample containers to be only connected and positioned to receive flow from one of the three openings and none of the remaining openings. It is further preferred that the second container holding means include threads of a first diameter to engage threads of one of the open top sample containers and threads of a second diameter to engage threads of another open top sample container, wherein said first and second diameters are different. It is further preferred that the second container holding means include threads on an outside surface of separate members extending outwardly from the bottom surface of the body to engage threads inside open top sample containers. It is further preferred that the second container holding means include threads on an outside surface of separate members extending outwardly from the bottom surface of the body to engage threads inside open top sample containers.

Another aspect of the invention is a device to collect liquid samples of compounds adsorbed on an extraction disc. The device includes a body including a top, a bottom with a bottom surface, and at least one side wall, with a cavity opening to the top of sufficient size and shape to receive and hold the extraction disc in a horizontal position. The device further includes first container holding means to hold an open bottom container on the top of the body and seal the open bottom around the cavity opening. The device also includes channeling means in the body under the extraction disc to channel liquid flow through the extraction disc to a single first passage in the body opening downwardly at an orifice. The device further includes three second passages in the body, each passage comprising an upper end and a lower end opening downwardly and first valve means to selectively direct liquid flow out of the orifice to the upper end of a chosen second passage. The device also includes second container holding means to hold an open top container on the bottom of the body and seal said open top over the bottom surface. The device further includes a third passage through the body from an opening on the side of the body connectable to a vacuum source, the passage continuing to an opening through the bottom surface of the body and second valve means to selectively open or close the third passage. The device also includes third container holding means to hold an open top sample container to the bottom of the body aligning said open top below the lower end of a first of the second passage and fourth container holding means to hold a second open top sample container to the bottom of the body aligning said open top below the lower end of a second of the second passage. The device further includes tubular means to channel flow out of the lower end of a third of the second passages past the sample containers to the open top container.

It is preferred that the first valve means include a circular rod post rotatable to chosen radial positions in the body with three fourth passages opening laterally through the post, wherein one end of each fourth passage is alignable with only one of the upper end openings of the second passages while at the same time an opposite end of the aligned fourth passage is aligned with the orifice from the channeling means. It is further preferred that the third container holding means include threads of a first diameter to engage threads of an open top container, the fourth container holding means include threads of a second diameter to engage threads of an open top container, wherein said first and second diameters are different. It is also preferred that the threads of the third container holding means and the threads of the fourth container holding means be male threads to engage threads inside open top containers. It is further preferred that the third container holding means and the fourth container holding means both include male threads to engage female threads inside the top of the open top sample containers.

Another aspect of the invention is a rack device to collect liquid samples of compounds with a plurality of extraction devices each including a body that includes a top comprising an inlet to receive liquid flow, a bottom comprising bottom surface, at least one side wall including two side wall surfaces on opposite sides of the body, and two horizontal grooves parallel to each other into the two side wall surfaces on opposite sides of the body, the grooves being at a same height. Each extraction device includes first container holding means to detachable hold an open top cylindrical container to the bottom of the body. The rack device includes a housing comprising a front, a rear, two side walls, a top wall angled upwardly and rearwardly to a height, and a rear wall extending upwardly above said height. The rack device further includes a plurality of elliptical holes through the top wall of a size and shape to receive and horizontally support sides of the open top cylindrical containers of the extraction devices in an upright position. The rack device also includes a rack panel attached to and extending frontwardly from an upper portion of the rear wall to a front edge, the rack panel having a thickness. The rack device further includes a plurality of notches opening to the front edge, each notch forming side edges of the rack panel extending from the front edge rearwardly. The distance between the side edges bounding the notches and the thickness of the rack panel are sufficient to allow the grooves in the body of one of the extraction devices to engage the side edges as the device is supported on the rack panel. It is preferred that the rack panel be angled upwardly and frontwardly.

Yet another aspect of the invention is a method of extracting chemical compound analytes from a water sample. The method includes providing a device to collect liquid samples of compounds adsorbed on an extraction disc. The device includes a body that includes a top, a cavity opening to the top of sufficient size and shape to receive and hold the extraction disc in a horizontal position to receive liquid flow, a bottom portion that includes a bottom surface. The device further includes first container holding means to hold an open bottom container on the top of the body and to seal the open bottom around the cavity opening. The device also includes channeling means in the body to selectively stop or channel liquid flow through the body to a chosen one of three openings through the bottom surface. The device further includes first container holding means to detachable hold an open top container to the bottom of the body and seal said open top over the bottom surface. The device also includes second container holding means to detachable hold at least a wash open top sample container and an elute open top sample container to the bottom surface of the body aligning each of said open tops to receive liquid flow from only one of the three openings through the bottom surface. The device further includes guide means to guide flow out of a remaining opening of the three openings through the bottom surface past the sample containers to the open top container, and vacuum means to selectively open a vacuum source to the open top container. The method further includes opening the vacuum source to draw a vacuum on the open top container and adding a wash solvent capable of dissolving any analytes to the cavity opening to wash the extraction disc. The method then includes selecting the channeling means to channel liquid flow through the body and out of one of the openings through the bottom surface into the wash open top sample container and allowing the collection of the solvent in the wash open top sample container. The method then includes selecting the channeling means to stop liquid flow and supplying the water sample to the cavity opening to flow through the extraction disc. The method then includes selecting the channeling means to channel liquid flow through the body out of the remaining opening through the bottom surface and allowing the collection of the water in open top container. The method then includes selecting the channeling means to stop liquid flow and adding a solvent capable of dissolving all analytes to the cavity opening to collect the analytes from the extraction disc. The method then includes selecting the channeling means to channel liquid flow through the body and out of the opening through the bottom surface into the elute open top sample container. The method then includes closing the vacuum source to release the vacuum on the open top container and detaching the first container holding means to remove the open top container from the bottom surface of the body. The method then includes detaching the second container holding means to remove the elute open top sample container.

BRIEF DESCRIPTION OF THE DRAWINGS

FIG. 1 is a top frontal right side perspective view of the apparatus of the present invention.

FIG. 2 is view similar to that of FIG. 1 with one device separated from the discard container for collection of the sample liquid vial and readying the device for the next test.

FIG. 3 is a perspective view of one of the devices illustrated in FIG. 1.

FIG. 4 is a cross-sectional view taken along line 4—4 of FIG. 3.

FIG. 4a is an enlarged elevational view of the control lever with the positions of the multiple passage valve indicated.

FIG. 4b is a cross-sectional view similar to that of FIG. 4 with the valve shaft partially cut away to show the wash position.

FIG. 5 is a cross-sectional view of a preferred embodiment taken a similar fashion to that of FIG. 4b with the valve shaft turned to illustrate collection of the elute sample.

FIG. 5a is an enlarged vertical cross-sectional view of a liquid collection cap as shown in FIG. 5.

FIG. 5b is an enlarged vertical cross-sectional view of a collection cap as shown in FIG. 5.

DESCRIPTION OF PREFERRED EMBODIMENTS

Figure 6:
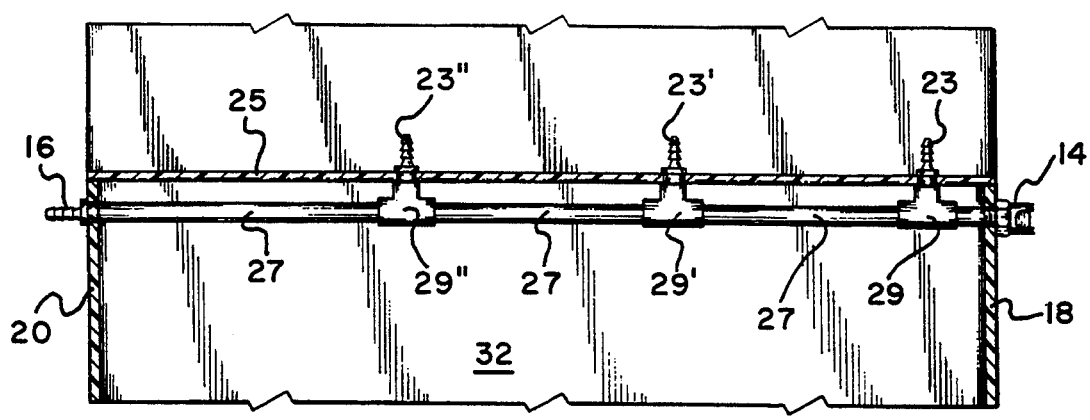
FIG. 6 is partial cutaway cross-sectional view taken along line 6—6 of FIG. 1.

In FIGS. 1 and 2, drawn on a scale of about one to six, three extraction devices 10 are supported in rack device 12 as further illustrated in the partial cross-sectional view of FIG. 6. Multiple rack devices 12 may be serially connected to a common vacuum source through female coupling 14 on right side wall 18 and male coupling 16 on left side wall 20. Couplings 14 and 16 are standard CPC couplings supplied by Colder Products Company, wherein the female coupling includes an automatic shutoff upon disconnect maintaining the vacuum pressure so long as the male coupling remains sealed off. Brochure describing coupling is incorporated by reference thereto. Rack 12 includes housing 22 constructed of three sixteenth inch thick impact resistant acrylic polymer sheet with the parts attached together with a suitable adhesive. Top wall 24 is angled upwardly and rearwardly about thirty degrees from the horizontal to aid in display of the liquid level in discard containers 26 which interfit into elliptical holes 28. Discard jars 26 have a one and one-quarter liter volume and are about four inches wide and nine inches high so that they loosely interfit into elliptical holes 28 which are four and a half inches by five and a quarter inches in diameter. The holes are positioned to support jars 26 in an upright position. Rail 30 adhered to the inside surface of the bottom wall of housing 22 provides a vertical support surface about two inches high immediately behind jars 26 to prevent them from tipping forwardly. Rear wall 32 extends upwardly about nine inches above top wall 24 on the top of which is adhered rack panel 34 constructed of one quarter inch thick plastic sheet. Notch openings 36 are cut about three and one quarter inches wide to allow the side edges 38 to engage grooves 40 cut into both sides of body 42 of device 10. For removal of elute container 44 and wash container 46 device 10 is disengaged from discard jar 26 lifted upwardly and slid into engagement into notch opening 36. Male coupler 48 connecting vacuum tubing 50 may be disengaged, as shown in FIG. 2, or may remain connected as device 10 is lifted upwardly and engaged and held on rack panel 34. Containers 44 and 46 may be screwed off with one hand while device 10 is held on rack panel 34 which is angled upwardly and forwardly about five degrees from the horizontal to aid in holding devices 10 in position. While device 10 is engaged in and held on rack panel 34 the apparatus provides easy access to open top and bottom graduated glass container 52 with a capacity of twelve hundred and fifty milliliters allowing easy removal for access to extraction disc 54. Container 52 should have a minimum capacity sufficient to easily receive standard samples of one liter. Similarly identical devices 10' and 10" are held in elliptical openings 28' and 28" respectively, each able to be disconnected and supported on rack panel 34 in notch openings 36' and 36" respectively.

As shown in FIG. 6, male couplers 23, 23' and 23" are connected to and extend through upper horizontal wall 25 inside housing 22. Horizontal vacuum tubing 27 connects male coupler 16 with female coupler 14 extending outwardly through opposite end walls of the housing. "T" connectors 29, 29' and 29" connect to male coupler 23, 23' and 23" respectively.

Figure 8:
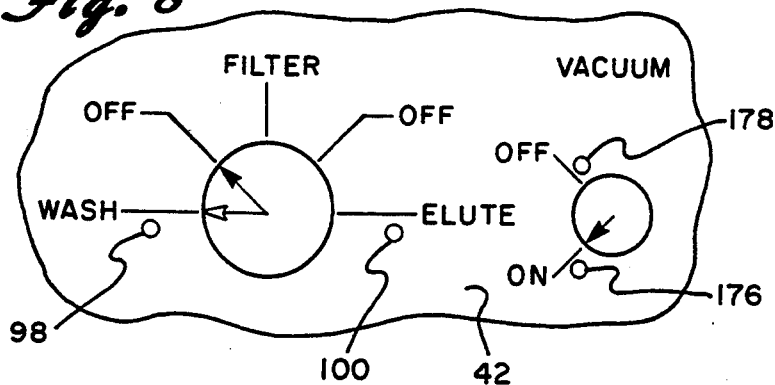
FIGS. 8, 8a, 8b, 8c illustrate the method and procedure steps involved in utilizing the apparatus illustrated in the preceding figures.

In FIG. 3, discard container 26 is exploded away from device 10 exposing threaded top opening 56 threadably disengaged from annular ring interlock 58. As shown in FIG. 4, drawn on a scale of about one to one and one-half, the shadow view of container 26 shows how the top edge of the container is sealed against bottom surface 60 of body 42 sandwiching annular lip 62 extending radially outwardly from the bottom edge of body 42. Container 52 with unobstructed top opening 64 rests plastic support ring of extraction disc 54 which is pressed on the top body 42 aligning unobstructed bottom opening 66. Threaded ring connect 68 engages external threads at the top raised edge of body 42 drawing downwardly on bottom lip 70 extending outwardly from the bottom edge of container 52 exerting pressure against the polymeric ring of disc 54 effecting a seal. Opening 72 in the side of connect 68 allows lip 70 to be inserted into ring connect 68 to be tightened in place. Hollowed out of body 42' that is constructed of TEFLON ® polytetrafluoroethylene polymer reinforced with glass fibers, is conically shaped opening 74 opening upwardly below extraction disc 54 and narrowing at the bottom to vertical passage 76 opening downwardly to the surface of cylindrical solid valve stem 80 positioned horizontally and rotatable to chosen radial positions. Valve stem 80 is machined out of DuPONT TEFZEL ® fluorocarbon resin and extends outwardly from the side of body 42 where handle 84 extending radially from stem 80 provides easy turning of the stem. TEFLON ® "O" ring 86 holds stem 80 into body 42. As shown in FIGS. 4 and 4a, stem 80 is positioned with handle 84 in a horizontal position with pointed stop pin 88 pointing upwardly to the designation "filter" ready to receive a one liter water sample aligning passage 90 cut transversely through stem 80 aligning the upper end of the passage with orifice 78 and the bottom end with top opening 92 of passage 94 through body 42 directly downwardly opening through bottom surface 60 into extension tube 96 opening below containers 44 and 46 directly into discard container 26. Stop pins 98 and 100 as shown in FIG. 8 extend outwardly from the side of body 42 providing a stop position for pointed/stop pin 88 in the "wash" and "elute" positions. As shown in FIG. 4b, valve stem 80 has been rotated clockwise ninety degrees as diagramed in FIG. 8b with pointer/stop pin 88 against stop pin 100 pointing to the designation "elute". In that position, passage 102 is aligned to open the top end of that passage with orifice 78 while the bottom end of passage 102 is in alignment and opens to the top end of passage 104 which in turn opens to vertical tube 106 extending downwardly into elute container 46 which is threadably engaged through bottom surface 60 of body 42 with threads 108. In this position, passage 90 is in a horizontal position and is inoperative while passage 110 is aligned with top 92 of passage 94, but the upper end is not in alignment with orifice 78 and is therefore inoperative. The preferred embodiment illustrated in FIG. 5 utilizes valve stem 80' which is identical in all respects to valve stem 80. Likewise identical elements are designated with the "prime" designation. The position of valve stem 80' illustrates the third position of the valve stem to complete the series begun with FIGS. 4 and 4b. In this position, stem 80' has been rotated one hundred and eighty degrees counter clockwise from the position illustrated in FIG. 4b. In this position, stop pin 88' is against stop pin 98 pointing to the designation "wash" as shown in FIG. 8. In this radial position, passage 110' is now in the operative position with the upper end aligned with orifice 78 at the bottom of passage 76 aligned with the bottom end of passage 110' aligned with the top end of passage 112' which is aligned vertically downwardly in body 114 opening to tube 128 opening to container 126. To that extent, the valve mechanism of FIG. 5 operates identically to that of the device of FIGS. 4 and 4b. In this embodiment, body 114 differs in its bottom section and in particular as to the container holding devices and tube dispensing mechanisms at the bottom of this modification of device 10. Connector member 116 is engaged through threads 118 at its upper end into the bottom of body 114. It is then pinned in position to insure that it is not inadvertently loosened. Lower section 120 of connector member 116 extends downwardly past bottom surface 60' of body 114 with external threads carved on the side of lower section 120 sized to threadably engage inside threads 122 of wash bottle container 126 threads 122 are about one-half inch in diameter. Passage 124 extends vertically through the center of connector member 116 opening at the top end to receive liquid flow through passage 112' and at the bottom end connecting to TEFLON ® dispensing tube 126. As more clearly shown in FIG. 5b, passage 124 quickly necks down to a flow restriction diameter approximating the inside diameter of dispensing tube 128 which is bent at a forty-five degree angle at its lower end to reduce any significant splashing in container 126. Wash container 126 is different from container 44 not only with its inside threads in the neck, but also having concave bottom surface 130 inside the container while having downwardly extending outer side walls to form flat base 132. In this embodiment, passage 104' opens downwardly into passage 134 extending vertically downwardly through connector member 136, best illustrated in FIG. 5a. Again, connector member 136 is threadably engaged through threads 138 into the bottom of body 42 and through bottom surface 60'. It is again pinned to insure maintenance of the seal. Bottom section 140 of member 136 extends downwardly past bottom surface 60' and has external threads around that bottom section. In this case, the diameter of these threads is about five eighth inch assuring that wash container 126 cannot be inadvertently attached to receive liquid through dispensing tube 144 which is connected directly into passage 134. As shown in FIG. 5, elute container 146 is threadably engaged through inside threads 148 with outside threads 142 on connector member 136. Container 146 also has concave bottom inside surface 140 with flange bottom 152 extending the outside walls downwardly to provide a flat resting surface. Another difference between body 114 and body 42, is cut out finger grips 154 on opposite sides of body 114. The cutouts are of the vertical upper walls and threads to expose the edges of extraction disc 54. This facilitates easy removal of the extraction disc by grasping it with two fingers through the cut outs in the wall.

Figure 7:
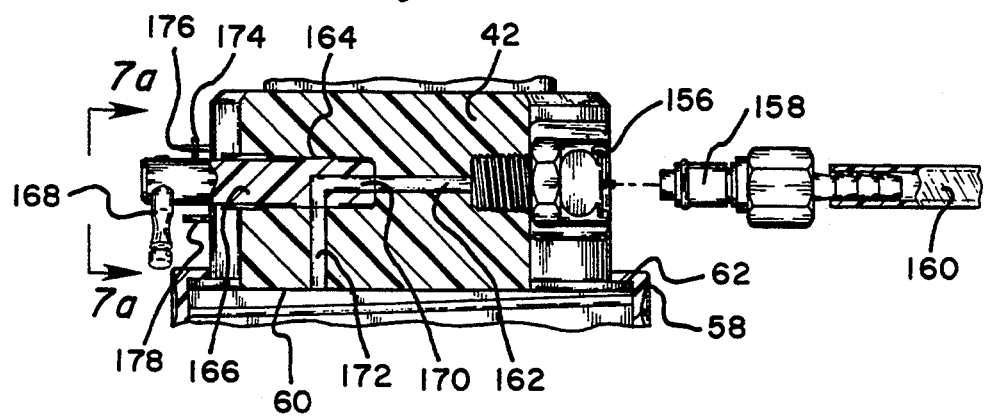
FIG. 7 is a partial cross-sectional view taken along line 7—7 of FIG. 3.
Figure 7A:
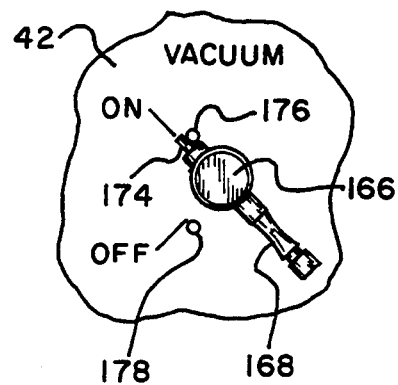
FIG. 7a is a side elevational view viewed from line 7a–7a of FIG. 7.

Vacuum to container 26 sealed against device 10 is controlled by the mechanism illustrated in FIG. 7. Female CPC coupling 156 from Colder Products Company is threadably engaged in the side wall of body 142 ready to receive male coupling 158 connected to vacuum tube 160 connectable to a vacuum source. Horizontal passage 162 through body 42 opens at one end to the opening through female coupler 156 and at the other end at the terminal end of bore 160 into which valve stem 166 is held. Stem 166 is rotatable radially positioned by handle 168. Passage 170 extends from the inside terminal end of stem 166 along its central axis to a point where the passage turns ninety degrees and continues laterally through the side surface of stem 166. At that point, it is rotatably alignable with vertical passage 172 through body 142 which at its upper end is alignable with passage 170 and at its lower end opens through bottom surface 60. Thus, when passage 170 is aligned such that it opens to passage 172, vacuum is drawn through passage 162 from the vacuum source. Control is accomplished by the radial position of stem 166 with alignment assured with pointer stop pin 174 which when abutted against stop pin 176 passage 170 is in alignment with passage 172 to provide vacuum. When stem 166 is rotated so that pin 174 is against stop pin 178, the operator can be assured that there is no alignment and vacuum to the system is off. The positions of pointer stop pin 174 are best illustrated in FIG. 7a and the FIG. 8 series. A full two-sided handle may be utilized with the pointer stop pin extending at a ninety degree angle from the handle.

Figure 8A:
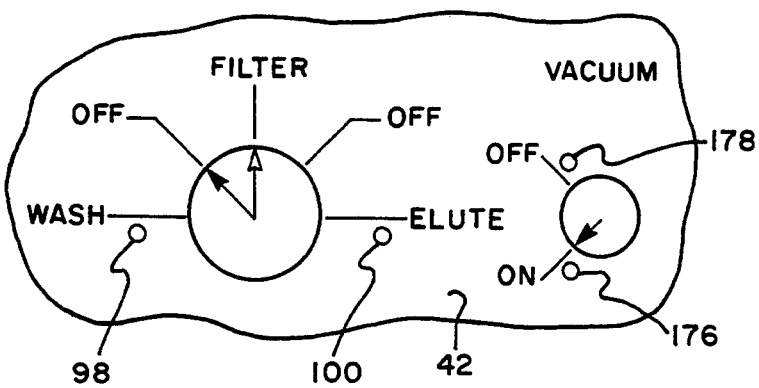
Figure 8B:
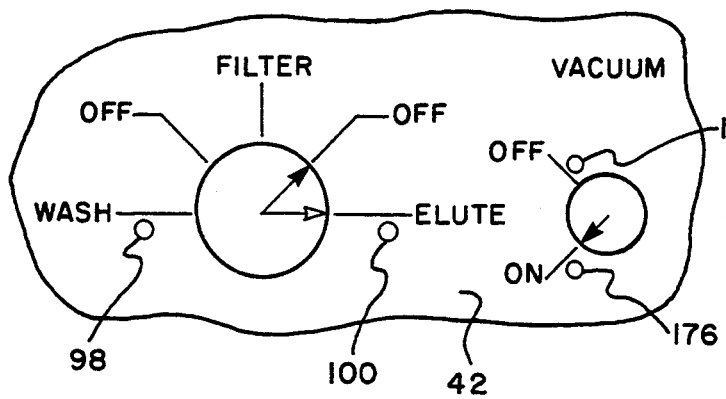
Figure 8C:
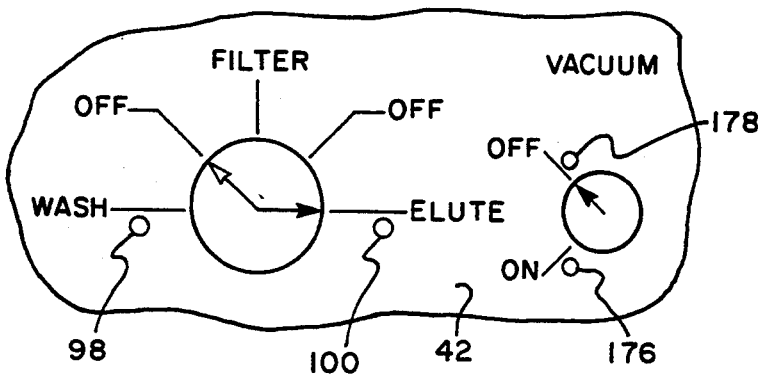

As illustrated in FIGS. 8, 8a, 8b, and 8c, the method of using the device shows the positioning of valve stems 80 and 166 to control the flow through the body and the vacuum to container 26. In each figure the "solid" arrow showing pointer pin 88 is the start position and the "open" arrow shows the position that stem 80 is moved to during the step. At the start, stem 80 is positioned with pointer pin 88 directed to the off position situated between the wash and filter positions. Stem 166 is rotated so that pointer 174 engages stop pin 176 drawing a vacuum on container 28 and the entire device. A final pre-wash, also known as the final eluting solvent, is added to container 52 and valve stem 80 is rotated to the "wash" position against stop pin 98. Reclaimed solvent is collected in the wash container. As shown in FIG. 8a, stem 80 is repositioned in the off position and the disc is pre-wetted with methanol immediately before adding the one liter sample of water to be tested to avoid allowing the disc to dry. After the sample has been added to container 52, valve 80 is positioned with pointer 88 directed to the designation "filter" allowing the water to pass through the extraction disc leaving the chemicals from the water adsorbed on the disc with the water flowing directly downwardly through tube 96 into collection container 26. The next step, as shown in FIG 8b, is to turn valve 80 into the "off" position located between the "filter" and the "elute" designations closing valve 80. The appropriate solvent to collect the analyte from the disc is added to container 52 and valve 80 is turned to direct pointer 88 at the designation "elute". The elute sample is collected in the elute sample container after which valve 166 is turned to direct pointer 174 against stop 178 to turn the vacuum off to container 26. Valve 80 is turned to the first "off" position and the device is ready for the next extraction.

While this invention has been described with reference to the specific embodiments disclosed herein, it is not confined to the details set forth and the patent is intended to include modifications and changes which may come within and extend from the following claims.

We claim:

1. A device to collect liquid samples of compounds comprising:
   (a) a body comprising an inlet to receive liquid flow and a bottom portion comprising a bottom surface,
   (b) channeling means in the body to selectively channel liquid flow through the body to a chosen one of three openings through the bottom surface,
   (c) an open topped container Comprising an open top, a bottom, and a sidewall extending upwardly from the bottom to the open top,
   (d) first container holding means to detachably hold the open topped container to the bottom of the body and seal said open top over the bottom surface,
   (e) second container holding means to hold at least two open top sample containers to the bottom surface of the body inside the open topped container aligning each of said open tops to receive liquid flow from only one of the three openings through the bottom surface,
   (f) guide means to guide flow out of a remaining opening of the three openings through the bottom surface past the sample containers to the open topped container, and
   (g) vacuum means to selectively open a vacuum source to the open topped container.

2. The device of claim 1 wherein the body further comprises a top and a cavity opening to the top of sufficient size and shape to receive and hold an extraction disc in a horizontal position.

3. The device of claim 2 wherein the device further comprises first container holding means to hold an open bottom container on the top of the body and to seal the open bottom around the cavity opening.

4. The device of claim 1 wherein the channeling means comprises a single first passage in the body from the inlet to an orifice opening to a first valve means to selectively direct liquid flow out of the orifice to a chosen opening to one of three second passages through the body, each of the second passages opening to one of the three openings through the bottom surface.

5. The device of claim 4 wherein the first valve means comprises a circular rod stem rotatable to chosen radial positions in the body with three passages laterally through the stem, wherein one end of each said passage is alignable with only one of the second passages while at the same time an opposite end of the aligned said passage is in flow connection with the first passage.

6. The device of claim 1 wherein the vacuum means comprises a third passage through the body from an opening on a side of the body connectable to a vacuum source, the passage continuing to an opening through the bottom surface of the body and vacuum valve means to selectively open or close the third passage.

7. The device of claim 1 wherein the second container holding means allows each of the open top sample containers to be only connected and positioned to receive flow from one of the three openings and none of remaining openings.

8. The device of claim 7 wherein the second container holding means comprises threads of a first diameter to engage threads of one of the open top sample containers and threads of a second diameter to engage threads of another open top sample container, wherein said first and second diameters are different.

9. The device of claim 8 wherein the second container holding means comprises threads on an outside surface of separate members extending outwardly from the bottom surface of the body to engage threads inside open top sample containers.

10. The device of claim 1 wherein the second container holding means comprises threads on an outside surface of separate members extending outwardly from the bottom surface of the body to engage threads inside open top sample containers.

11. A device to collect liquid samples of compounds adsorbed on an extraction disc, the device comprising:
 (a) a body comprising a top, a bottom with a bottom surface, and at least one side wall, with a cavity opening to the top of sufficient size and shape to receive and hold the extraction disc in a horizontal position,
 (b) first container holding means to hold an open bottom container on the top of the body and to seal the open bottom around the cavity opening,
 (c) channeling means in the body under the extraction disc to channel liquid flow through the extraction disc to a single first passage in the body opening downwardly at an orifice,
 (d) three second passages in the body, each passage comprising an upper end and a lower end opening downwardly,
 (e) first valve means to selectively direct liquid flow out of the orifice to the upper end of a chosen second passage,
 (f) second container holding means to hold an open topped container on the bottom of the body and seal said open top over the bottom surface,
 (g) a third passage through the body from an opening on the side of the body connectable to a vacuum source, the passage continuing to an opening through the bottom surface of the body,
 (h) vacuum valve means to selectively open or close the third passage,
 (i) third container holding means to hold a first open top sample container to the bottom of the body aligning said open top below the lower end of a first of the second passages,
 (j) fourth container holding means to hold a second open top sample container to the bottom of the body aligning said open top below the lower end of a second of the second passages, and
 (k) tubular means to channel flow out of the lower end of a third of the second passages past the sample containers to the open top container.

12. The device of claim 11 wherein the first valve means comprises a circular rod stem rotatable to chosen radial positions in the body with three fourth passages laterally through the stem, wherein one end of each fourth passage is alignable with only one of the upper end openings of the second passages while at the same time an opposite end of the aligned fourth passage is aligned with the orifice from the channeling means.

13. The device of claim 11 wherein the third container holding means comprises threads of a first diameter to engage threads of an open top container and the fourth container holding means comprises threads of a second diameter to engage threads of an open top container, wherein said first and second diameters are different.

14. The device of claim 13 wherein the threads of the third container holding means and the threads of the fourth container holding means comprise male threads to engage threads inside open top containers.

15. The device of claim 13 wherein the third container holding means and the fourth container holding means both comprise male threads to engage female threads inside the top of the open top sample containers.

16. A device to collect liquid samples of compounds comprising:
 (a) a body comprising an inlet to receive liquid flow and a bottom portion comprising a bottom surface,
 (b) channeling means in the body to selectively channel liquid flow through the body to a chosen one of three openings through the bottom surface,
 (c) first container holding means to detachably hold an open top container to the bottom of the body and seal said open top over the bottom surface,
 (d) second container holding means to hold at least two open top sample containers to the bottom surface of the body aligning each of said open tops to receive liquid flow from only one of the three openings through the bottom surface,
 (e) guide means to guide flow out of a remaining opening of the three openings through the bottom surface past the sample containers to the open top container, and
 (f) vacuum means to selectively open a vacuum source to the open top container,
 wherein the vacuum means comprises a third passage through the body from an opening on a side of the body connectable to a vacuum source, the passage continuing to an opening through the bottom surface of the body and vacuum valve means to selectively open or close the third passage.

17. The device of claim 16 wherein the second container holding means comprises threads of a first diameter to engage threads of one of the open top sample containers and threads of a second diameter to engage threads of another open top sample container, wherein said first and second diameters are different.

18. The device of claim 16 wherein the second container holding means comprises threads on an outside surface of separate members extending outwardly from the bottom surface of the body to engage threads inside open top sample containers.

19. The device of claim 18 wherein the second container holding means comprises threads on an outside surface of separate members extending outwardly from the bottom surface of the body to engage threads inside open top sample containers.

20. A device to collect liquid samples of compounds comprising:
   (a) a body comprising an inlet to receive liquid flow and a bottom portion comprising a bottom surface,
   (b) channeling means in the body to selectively channel liquid flow through the body to a chosen one of three openings through the bottom surface, said channeling means comprising first valve means comprising a circular rod stem rotatable to chosen radial positions in the body with three passages laterally through the stem,
   (c) first container holding means to detachably hold an open top container to the bottom of the body and seal said open top over the bottom surface,
   (d) second container holding means to hold at least two open top sample containers to the bottom surface of the body aligning each of said open tops to receive liquid flow from only one of the three openings through the bottom surface,
   (e) guide means to guide flow out of a remaining opening of the three openings through the bottom surface past the sample containers to the open top container, and
   (f) vacuum means to selectively open a vacuum source to the open top container,
   wherein one end of each said passage through the stem is in flow connection with only one of the three openings through the bottom surface while at the same time an opposite end of the aligned said passage is in flow connection with the inlet to the body.

21. The device of claim 20 wherein the second container holding means comprises threads of a first diameter to engage threads of one of the open top sample containers and threads of a second diameter to engage threads of another open top sample container, wherein said first and second diameters are different.

22. The device of claim 20 wherein the second container holding means comprises threads on an outside surface of separate members extending outwardly from the bottom surface of the body to engage threads inside open top sample containers.

23. The device of claim 22 wherein the second container holding means comprises threads on an outside surface of separate members extending outwardly from the bottom surface of the body to engage threads inside open top sample containers.

* * * * *